(12) United States Patent
Weiss et al.

(10) Patent No.: US 6,437,357 B1
(45) Date of Patent: Aug. 20, 2002

(54) GLASS INSPECTION SYSTEM INCLUDING BRIGHT FIELD AND DARK FIELD ILLUMINATION

(75) Inventors: Adam Weiss, Pickering; Alexandre Obotnine, Willowdale, both of (CA)

(73) Assignee: Photon Dynamics Canada Inc., Markham (CA)

( * ) Notice: Subject to any disclaimer, the term of this patent is extended or adjusted under 35 U.S.C. 154(b) by 0 days.

(21) Appl. No.: 09/430,499

(22) Filed: Oct. 29, 1999

(30) Foreign Application Priority Data

Oct. 30, 1998 (CA) ............................................. 2252308

(51) Int. Cl.[7] ............................................. G01N 21/88
(52) U.S. Cl. ............................. 250/559.4; 250/559.46; 250/223 R; 356/237.1; 356/239.1; 356/430
(58) Field of Search ........................ 250/559.4, 559.41, 250/559.42, 559.43, 559.44, 559.45, 559.46, 223 R; 356/237.1, 239.1, 239.2, 239.7, 239.8, 237.2, 429, 430

(56) References Cited

U.S. PATENT DOCUMENTS

| | | | |
|---|---|---|---|
| 3,737,665 A | | 6/1973 | Nagae |
| 4,492,477 A | | 1/1985 | Leser |
| 4,583,854 A | | 4/1986 | Lozar |
| 4,641,966 A | | 2/1987 | Lemmers et al. |
| 5,459,330 A | | 10/1995 | Venaille et al. |
| 6,011,620 A | | 1/2000 | Sites et al. |
| 6,144,446 A | * | 11/2000 | Nagasaki et al. ......... 356/239.8 |

FOREIGN PATENT DOCUMENTS

| | | |
|---|---|---|
| CA | 2252308 | 10/1998 |
| DE | 3926349 A1 | 8/1989 |
| DE | 41 39 094 | 11/1991 |
| DE | 198 09 505 | 3/1998 |
| EP | 0 317 638 | 5/1989 |
| EP | 0 559 916 | 9/1992 |
| GB | 1 526 930 | 12/1974 |
| JP | 08327561 A | * 12/1996 |
| WO | WO 96/05503 | 2/1996 |
| WO | WO 00/26647 | 5/2000 |

OTHER PUBLICATIONS

Patent Abstracts of Japan, publication No. 04157344.
Patent Abstracts of Japan, vol. 1997, No. 04, Apr. 30, 1997, for: JP 08 327561 A, Dec. 13, 1996.
Patent Abstracts of Japan, vol. 016, No. 468, Sep. 29, 1992, for: JP 04 168251, Jun. 16, 1992.
Patent Abstracts of Japan, vol. 1996, No. 11, Nov. 29, 1996, for: JP 08 193955, Jul. 30, 1996.
International Search Report for: PCT/CA99/00953, completed: Dec. 20, 1999.

* cited by examiner

*Primary Examiner*—Kevin Pyo
(74) *Attorney, Agent, or Firm*—Merchant & Gould P.C.

(57) ABSTRACT

An inspection system for a sheet of glass. The system comprises a first laser and a second laser, each of which provide a sheet of light, a cylindrical lens system, and a first light detection system and a second light detection system. The first laser is located at the focal point of the lens system. The second laser is located at a distance from the lens system that is greater than that of the first laser, and off of the axis of the lens system. The first light detection system receives light from the first laser and the second light detection system receives light from the second laser. The inspection system is adapted to position a sheet of glass between the lens system and the detection systems. A method is also described.

50 Claims, 4 Drawing Sheets

GLASS INSPECTION SYSTEM INCLUDING BRIGHT FIELD AND DARK FIELD ILLUMINATION

FIELD OF THE INVENTION

The present invention relates to a non-contact inspection system for detection and identification of defects in sheets of glass, especially flat automotive glass. The system is intended to operate on a continuous production line at line speed, and for the identification of a wide variety of types of defects, including bubbles, scratches, chips, cracks and edge defects.

BACKGROUND OF THE INVENTION

In processes for manufacture of glass in sheet form, it is necessary to be able to inspect the sheets of glass for defects. Such defects may be in the form of scratches, bubbles, chips, blemishes and a wide variety of other defects. However, the mere detection of defects is insufficient in that the manufacturer of the sheet glass needs to know whether the defects are insignificant (i.e. minor in nature) and thus acceptable to the customer, or significant (i.e. a major flaw) such that the sheet glass would not conform to specifications established by the customer.

It is possible to use visual inspection of sheets of glass to identify those sheets that have defects. In addition, using visual inspection, it is possible to identify the location and possibly the type of defect. However, visual inspection is not acceptable because of the time and cost involved in conducting a visual inspection, and the limitations of such a method. It would be preferable to be able to conduct the inspection on-line in the production process, at production speeds, so that defects could be rapidly identified and communicated to production personnel and/or the sheets with the defects could be readily and quickly separated from sheets meeting quality specifications in an effective manner.

Methods have been developed for the inspection of sheets of glass using optical techniques. However, such methods have been limited in application, often only capable of identifying a small number of types of defects, and not capable of detecting and identifying the type, magnitude and location of a wide variety of defects. It is therefore an object of the present invention to provide a novel glass inspection system and method.

SUMMARY OF THE INVENTION

Apparatus and a method have now been found that are particularly intended for use in inspection of sheets of glass in a production line, at production speeds, in a manner that shows the magnitude, type and location of the defects in the sheet of glass, and especially intended to be an integral part of a glass processing system.

Accordingly, one aspect of the present invention provides an inspection system for a sheet of glass, comprising:
a) a first laser and a second laser, each of the first laser and second laser providing a sheet of light;
b) a cylindrical lens system, said lens system having a focal point on the main optical axis thereof;
c) a first light detection system and a second light detection system;
the first laser being located at the focal point of the lens system, the second laser being located at a distance from the lens system that is greater than that of the first laser, said second laser being located off of the axis of the lens system,
the first light detection system receiving light from the first laser and the second light detection system receiving light from the second laser, and providing information on the variation in intensity of light;
the inspection system being adapted to position and detect a sheet of glass between the lens system and the detection systems.

In preferred embodiments of the apparatus of the present invention, the system additionally comprises a computer executing software that utilizes information from the first and second light detection systems to determine the location, type and magnitude of defects in the sheet of glass.

Preferably, the computer records the location, type and magnitude of defects in the sheets of glass and displays the defects as a defect map on a computer monitor.

In a preferred embodiment, there are at least two first lasers and at least two second lasers, preferably with at least two cylindrical lens systems wherein each of the first lasers is located at the focal point of a respective cylindrical lens system and each of the second lasers is located at a distance from a respective cylindrical lens system that is greater than that of the first lasers, each second laser being located off of the axis of the respective cylindrical lens system, the first and second lasers being positioned such that light from both of the first lasers is detected by the first light detection system and light from both of the second lasers is detected by the second light detection system.

Another aspect of the present invention provides an inspection system for a sheet of glass, comprising:
a) a source of light to provide bright field illumination and means to detect said bright field illumination and variations therein; and
b) a source of light to provide dark field illumination and means to detect the dark field illumination and variations therein.

A further aspect of the present invention provides a method for inspection of a sheet of glass, comprising:
a) providing bright field illumination of a sheet of glass and detecting said bright field illumination thus obtained;
b) providing dark illumination of a sheet of glass and detecting said dark field illumination thus obtained; and
c) analyzing said bright field and dark field illumination for presence of defects in said sheet of glass.

In a preferred embodiment of the method of the invention, the illumination is analyzed using computer software.

In another embodiment, the inspection system is tuned to detect defects having a size of greater than 100 microns, but not recognize smaller defects e.g. dust.

An additional aspect of the invention provides a method for inspection of a sheet of glass for defects therein, in apparatus comprising:
a) a first laser and a second laser, each of the first laser and second laser providing a sheet of light;
b) a cylindrical lens system, said lens system having a focal point on the main optical axis thereof;
c) a first light detection system and a second light detection system;
passing light from the first laser located at the focal point of the lens system and from the second laser located at a distance from the lens system that is greater than that of the first laser through said lens system, said second laser being located off of the axis of the lens system, the light from the first laser being collimated light,
passing said light through a sheet of glass to be inspected; and detecting light from the first laser with the first light detection system and variations therein; and detecting light from the second laser with the second light detection system and variations therein.

BRIEF DESCRIPTION OF THE DRAWINGS

The present invention is illustrated by the embodiments shown in the drawings, in which.

DETAILED DESCRIPTION OF THE PREFERRED EMBODIMENTS

Techniques for the manufacture of glass are known. For example, glass may be converted to a molten state and then cast onto molten tin metal so that glass with a smooth surface may be obtained. Nonetheless, the glass that has been cast may be subject to a number of defects, including the presence of bubbles, dirt, stones, tin-drip distortion and other defects. Some such defects might arise from raw materials fed to the process while other defects will arise from processing problems, including incorrect temperature or other process parameters and aging of apparatus, especially of kilns or other apparatus used in the heating of the glass.

Subsequent to the casting of the glass, the glass is cut into sheets and then transferred to a manufacturer of glass articles for a particular enduse. In the automobile industry, for instance, the glass articles could be the windows of the vehicle, in which event the manufacturer will shape the glass to a particular size and configuration, prepare ground edges to the glass, cut holes in the glass in locations as required, imprint logos or other writing in the glass and otherwise process the cut glass to a predetermined set of specifications. Despite care in operation of the process, the various steps can result in the formation of chips, cracks, scratches, and other defects that might render the glass unacceptable to a customer. The manufacturer must be able to detect the defects, and separate sheets of glass conforming to specification from those that do not.

Examples of some of the defects that may be present in a sheet of glass that is being prepared for use in, for instance, the automobile industry, include bubbles i.e. inclusion of gas in the glass in a generally spherical shape, blisters i.e. elongated bubbles, seeds i.e. minute bubbles, dirt, lint, shell chips i.e. small pieces of glass broken away from the main body of the glass, stones, strands i.e. very fine, string-like pieces of foreign matter embedded in the glass or laminates thereof, vents i.e. small cracks usually appearing at the corners of cut glass, pits or digs i.e. small hollows and other defects.

While the glass is generally described herein as a sheet of glass, it is to be understood that in many instances the glass is in the form of a laminated or tempered glass or other glass, to give it strength, shatter resistance or other properties. The processes used to form such glass may add to the potential defects in the sheet of glass.

Figure 1:
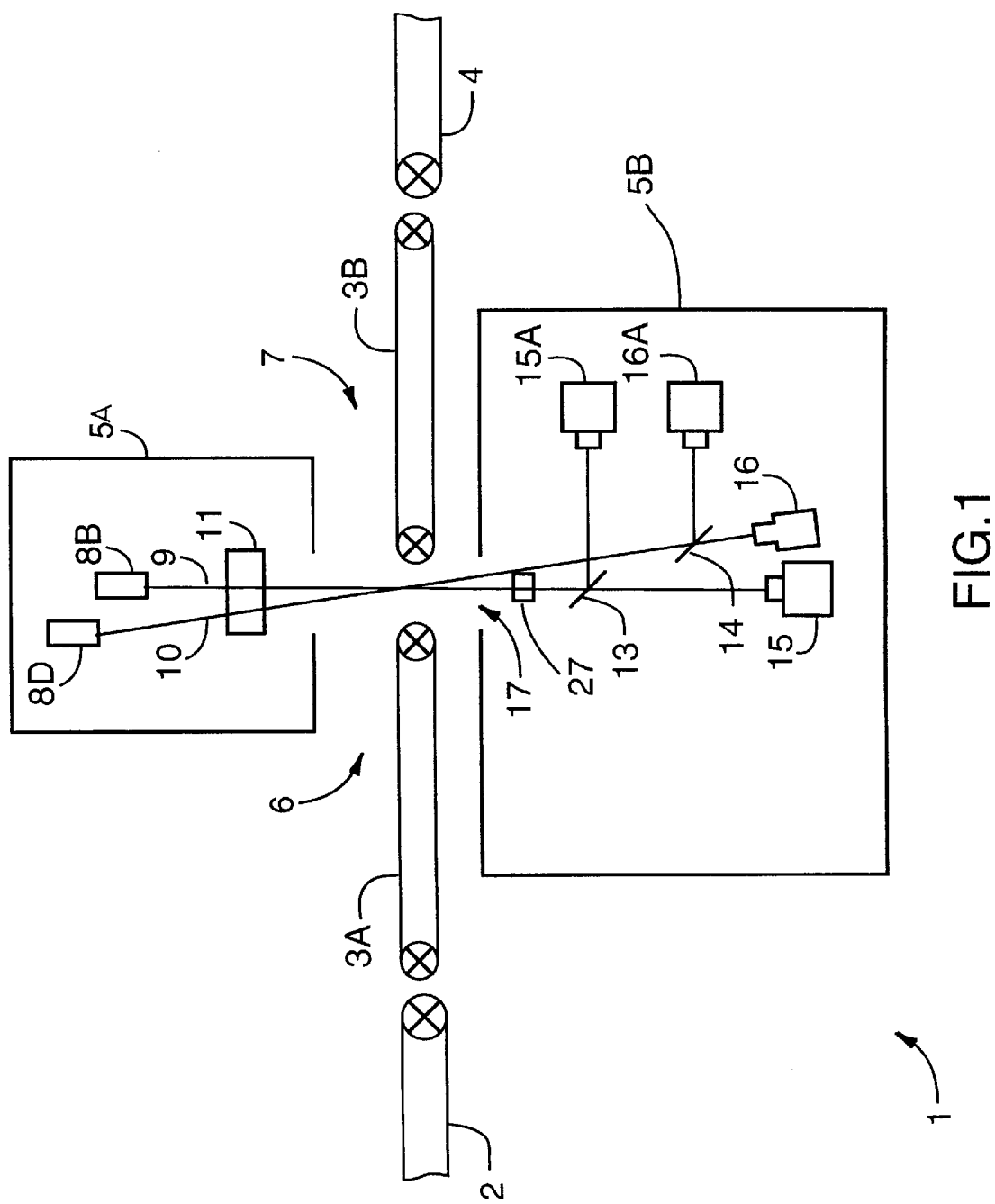
FIG. 1 is a schematic representation of a glass inspection apparatus in accordance with the present invention.

FIG. 1 shows a glass inspection system in accordance with the present invention, generally indicated by reference numeral 1. As illustrated in FIG. 1, glass inspection system 1 is located between an entry conveyor and an exit conveyer 4, both of which would normally be part of the production line in a plant for production of glass sheets. The glass inspection system 1 has an inspection conveyor that is formed in two parts, namely inspection conveyors 3A and 3B, each of which is of a size to support and transport a piece of glass to be inspected, as discussed herein. Inspection conveyor extends through a housing 5 having a housing entrance 6 and a housing exit 7. Sheets of glass to be inspected travel along entry conveyor onto inspection conveyer 3A, through the housing 5, onto inspection conveyor 3B and then onto exit conveyor 4. Entry conveyor 2 and exit conveyer 4 are shown as outside housing 5, but could extend into housing 5. Housing 5 consists of two separate parts, namely an upper housing 5A and a lower housing 5B. Housing 5 accommodates an optical system 8 (best seen in FIG. 2) that includes a pair of laser beam generating systems and a pair of light detection systems, each laser beam generating system being associated with a respective light detection system.

Upper housing 5A accommodates the pair of laser beam generating systems, generally identified by reference numeral 9. As can be seen, each laser beam generating system includes a laser 20 and 21 respectively. Each of laser 20 and 21 has a laser line generator associated therewith, that is preferably provided as an integral part of the laser. In particular, each laser and laser line generator are a sealed unit, and such sealed units are commercially available.

Laser 20 generates by means of the laser line generator, a diverging sheet of light, typically with a fan angle of 45° and adjusted to project a line approximately 100 $\mu$m in thickness and 450 mm in width. Laser 21 generates a converging sheet of light focused at the associated light detection system. The sheets of light are designated by reference numerals 22 and 24 respectively.

The sheet of light 22 generated by laser 20 is converted to a collimated sheet of light by a cylindrical lens system 11. The collimated sheet of light 22 is obtained by placing the laser 20, including the laser line generator, at the focal point of the cylindrical lens system 11. It is understood that the focal point is on the main optical axis of the cylindrical lens system 11. The collimated sheet of light 22 provides bright field illumination as will be discussed herein.

The laser line generator of laser 21 is located further from the cylindrical lens system 11 than that of laser 20 and is off of the main optical axis of the cylindrical lens system. Location of the laser line generator of laser 21 further away from the cylindrical lens system 11 as well as off of the focal point of cylindrical lens system 11 results in the sheet of light 24 not being collimated. The non-collimated sheet of light 24 provides dark field illumination as will be described herein.

The gap between the inspection conveyors 3A and 3B defines a light window 17 therebetween to allow the sheets of light 22 and 24 to pass from the upper housing 5A to the lower housing 5B. Light window 17 is typically 6–10 inches in width. Each of the inspection conveyors 3A and 3B is preferably a rubber conveyor, with each being of a size to fully accommodate the sheet of glass to be inspected, and operated to provide smooth passage of the sheet of glass through the housing 5 and hence, sheets of light 22 and 24. In particular, the length and width of the inspection conveyors 3A and 3B are customized to the particular use of the glass inspection system 1. It is important with respect to obtaining high quality images of defects that such smooth passage be provided. Thus, it is preferred that a single servo-motor drive both inspection conveyors, and that the speed of the inspection conveyors 3A and 3B be matched to the speed of the input and exit conveyors 2 and 4 respectively, to eliminate as much as is practical the risk of scratching of glass as the glass travels between conveyors. The inspection conveyors 3A and 3B should have an independent electrical circuit, so that the inspection conveyors will continue to operate in the unlikely event of electrical failure in the glass inspection system.

Lower housing 5B accommodates the pair of light detection systems, generally identified by reference numeral 16. Each light detection system is associated with a respective one of the laser generating systems 9. The light detection system associated with the laser generating system that generates sheet of light 22 includes a lens assembly 27, a mirror 28 and a light detector in the form of a camera 30A. In practice, the mirror 28 is provided to fold the sheet of light 22 so that the camera 30A may be conveniently located within the lower housing 5B. The light detection system associated with the laser generating system that generates sheet of light 24 includes a mirror 29 and a light detector in the form of a camera 31A. Although the light detection systems 16 are shown including the folding mirrors 28 and 29, those of skill in the art will appreciate that other optical arrangements can be used. For example, the cameras 30A and 31A can be positioned within the lower housing 5B in line with the lasers 20 and 21 respectively as shown by the dotted lines, thereby to obviate the need for the folding mirrors.

Camera 30A and camera 31A are connected to a computer system 36 via interface hardware 38. The computer system 36 executes suitable software for analysis of the sheets of light 22 and 24, and for computation of the visual quality of the sheet of glass. In particular, the software computes the type, magnitude and location of defects in the sheet of glass, using image information obtained from the cameras 30A and 31A. It is to be understood that the cameras do not merely record an average light intensity, but rather record detail provided in the sheets of light received by the cameras and the variation therein.

Figure 2:
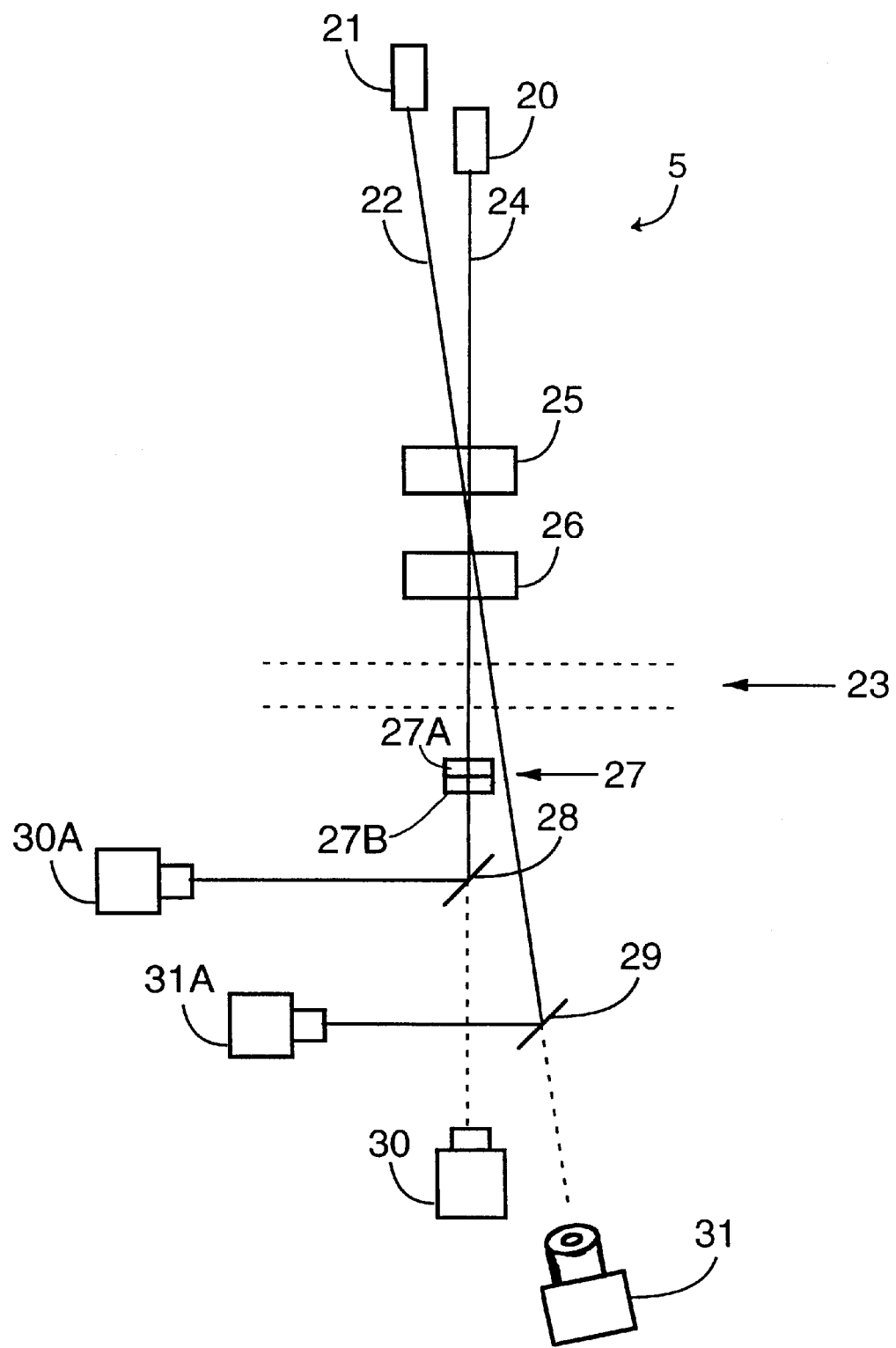
FIG. 2 is a schematic representation of a side view of an optical system forming part of the glass inspection apparatus of FIG. 1.

FIG. 2 better illustrates the optical system. As described above laser 20 and laser 21 each generate a sheet of light 22 and 24 respectively. Sheet of light 22 is referred to herein as bright field illumination. Sheet of light 24 is referred to herein as dark field illumination. The bright field illumination 22 is shown as passing perpendicularly toward the location of the glass sheet, whereas the dark field illumination 24 is shown as being disposed at a small angle to the perpendicular e.g. 4°, to prevent parasitic reflections of laser light. Both dark field illumination 24 and the bright field illumination 22 pass through the cylindrical lens system 11, which as shown includes lenses 25 and 26.

The laser 20, as mentioned previously, is located at the focal point of the cylindrical lens system 11, and consequently on the main optical axis of the cylindrical lens system. As a result, the bright field illumination 22 subsequent to the cylindrical lens system 11 is collimated. The laser 21 is located further away from the cylindrical lens system 11 than the laser 20, and off of the main optical axis of the cylindrical lens system. As a result, the dark field illumination 24 subsequent to the cylindrical lens system 11 is not collimated.

After passing through the glass sheet carried by the inspection conveyors 3A and 3B and through the light window 17, the bright field illumination 22 is projected onto the lens assembly 27. Lens assembly 27 has a ground glass screen 27A on its upper face, as viewed, and a fresnel lens 27B on its lower face. The focal length of the fresnel lens 27B is approximately equal to the distance between the camera 30A and the ground glass screen 27A. After passing through the lens assembly 27, the bright field illumination 22 is folded by mirror 28 and directed towards the camera 30A.

Dark field illumination 22 bypasses the lens assembly 27 and is reflected by mirror 29 towards camera 31A. A spatial filter 31 B in the form of an opaque dot is concentrically placed on the objective lens of the camera 31A to inhibit the most intense part of the sheet of light 24 from being received by the camera 31A.

Figure 3:
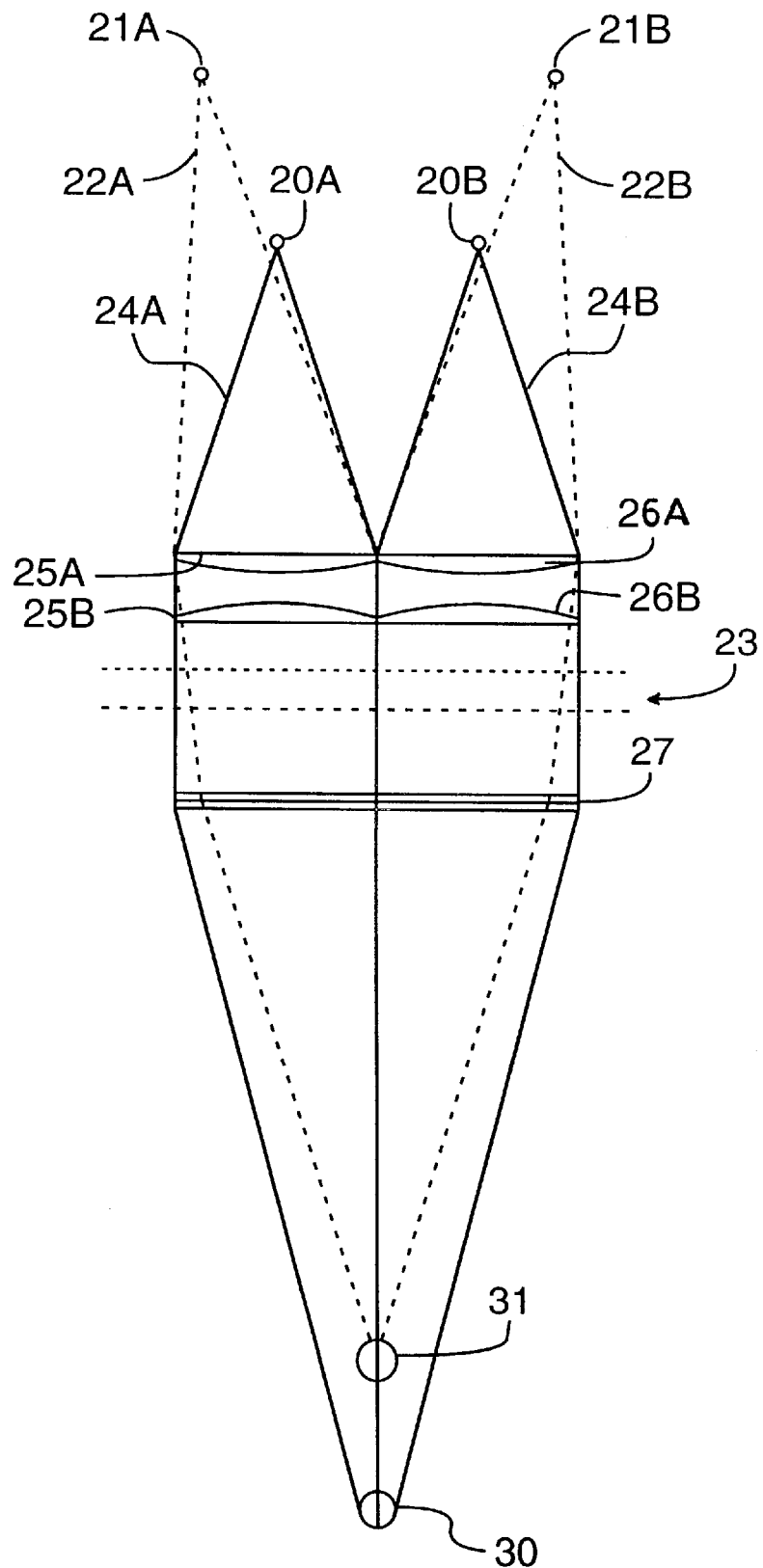
FIG. 3 is a schematic representation of an end view of an alternative optical system including dual bright field and dark field lasers.

FIG. 3 shows an end view of an alternative embodiment of an optical system similar to that described with respect to FIG. 2, but showing the use of two bright field lasers 20A and 20B and two dark field lasers 21A and 21B, to provide for inspection of a wide sheet of glass. The two bright field lasers, 20A and 20B, provide sheets of light 22A and 22B, shown in solid lines for clarity. The sheets of light are passed through a dual cylindrical lens system having sections 25A/25B and 26A/26B. It is understood that sections 25A and 25B are aligned with polished and bonded common faces so that there is minimal interference to the quality of the laser light resulting from the bonding of the sections. Sections 26A and 26B are similarly bonded. The sheets of light 22A and 22B subsequent to the cylindrical lens system 25/26 are collimated. The collimated sheets of light 22A and 22B pass through the glass sheet 23 to the lens assembly 27. From the lens assembly 27, the sheets of light are received by a camera 30. Camera 30 is focused on the surface of the ground glass screen of lens assembly 27.

The dark field lasers 21A and 21 B provide sheets of light 24A and 24B. These sheets of light are also passed through the cylindrical lens system. However, as dark field lasers 21A and 21B are not at the focal point of the cylindrical lens system and are off of its optical axis, the sheets of light are not collimated. After passing through the sheet of glass 23 and the light window 17, the sheets of light 24A and 24B are received by a camera 31. The converging sheets of light are focused at the center of the objective lens of camera 31. The focused light is blocked with a spatial filter in the form of an opaque dot attached to the center of the objective lens of camera 31.

Figure 4:
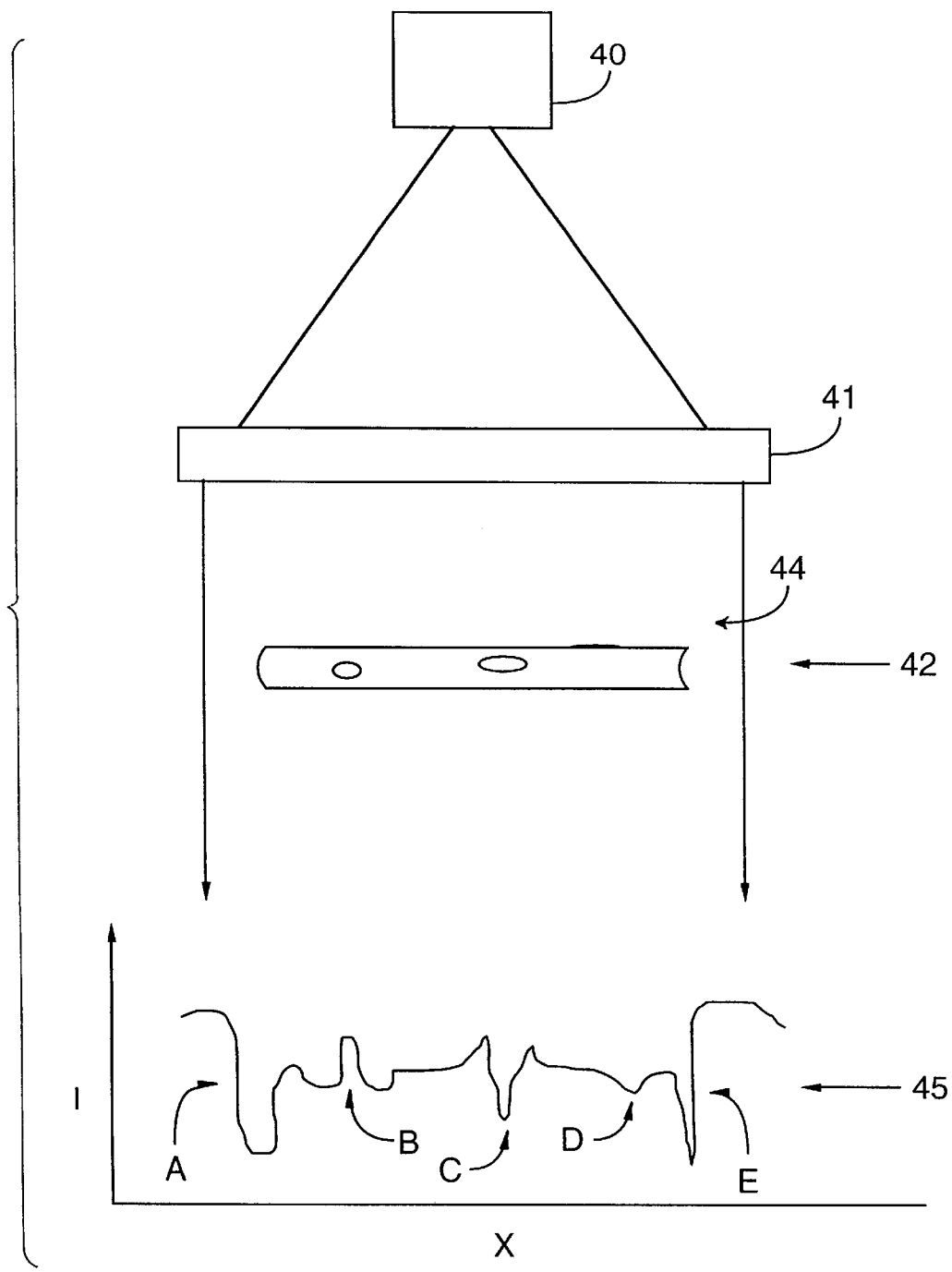
FIG. 4 is a schematic representation of inspection of a sheet of glass with defects, and spectra obtained.

FIG. 4 shows a laser 40 and a cylindrical lens system 41. A sheet of glass 42 having defects is located in the path of the collimated sheet of light 44 after it exits the cylindrical lens system 41. Light intensity variation 45 is produced in the collimated sheet of light 44 after it is passed through sheet 42. The defects represented in the sheet of glass 42 are, from the left, intended to represent a ground edge, a cold glass inclusion, a bubble, a surface contamination and broken glass. The light intensity variation, 45, correspondingly shows the ground edge of the glass, A, the cold glass inclusion, B, the bubble C, the surface contamination D and broken edge E. As discussed herein, defects tend to exhibit characteristic signatures indicating type and size of the defect. The light intensity variation also shows the edge of the sheet of glass, and will indicate the shape and other characteristics of the edge.

The present invention provides a glass inspection system that is capable of automation, and which utilizes laser optics and a computer visionbased system.

The glass inspection system utilizes a combination of laser illumination techniques using a structured light system that includes bright and dark field illumination, as well as high-resolution photodiode CCDs (charge coupled devices).

In preferred embodiments of the invention, the combination provides an advanced image analysis with exceptional inspection accuracy e.g. between 10 $\mu$m and 100 $\mu$m, as well as the capability to detect and differentiate a wide variety of defects including scratches, bubbles, chips, blemishes and other defects, and identifies the location, type and magnitude of the defects. The glass inspection system is capable of being operated at high-speeds e.g. at lines speeds of up to 0.3 m/sec, or higher. Thus, the glass inspection system may be used in-line in many manufacturing processes.

The software executed by the computer system 36 in the glass inspection system may be featured with a menu-based graphical user interface for ease of use, pass/fail specification changes and new model set ups, as well as automatic change over and calibration of the glass inspection system.

In a preferred embodiment, a standard user interface screen with a defect map is used, having colored icons that represent various types of defects. For examples, circles may be used to represent bubbles, squares to represent chips, triangles to represent scratches and so on. The icons may be made to appear at the actual x,y co-ordinates where the defects are located in the sheet of glass. In addition, the icons may be colored coded to represent the size of the defects e.g. the icons could be green to represent a very small defect, yellow to represent a medium defect and red to represent a large defect or reject. Moreover, the software provides characteristics of the defect, including type, size and location when the user "clicks" on the displayed icon representing that defect. 3-D visualization and mapping of the defects is also possible. Removable surface contaminants such as dust and water, may or may not be not detected by the glass inspection system, depending on the particular application of the glass inspection system.

The electronic hardware 38 interfaces the light detection systems and the computer system 36. This hardware 38 provides for control of the light detection systems, collection of pixel data from the light detection systems, compression of the pixel data by relaying for further processing only pixel data that is related to areas of interest in the glass sheet, and for pre-processing of pixel data by applying multi-level thresholds and marking transitions between different levels of intensities. A dedicated Digital Signal Processor (DSP) may be used to further process the pixel data. The processed pixel data may then be transmitted to the computer system 36 for the purpose of visualization and control, as discussed herein.

The interfacing hardware 38 may be set to recognize a threshold of illumination that indicates the presence of glass. A further threshold may be recognized for defects that prevent the passage of light e.g. permit less light to pass through than normally would occur for a piece of glass. In addition, a third upper threshold may be recognized, which corresponds to the presence of the edge effects of bubbles, as discussed herein. The upper and lower thresholds may be set at levels that represent defects that are unacceptable in glass, but not recognize defects that would pass specification. The interfacing hardware 38 may conveniently be operated to recognize transactions through any of these thresholds, and to recognize those that represent defects that are unacceptable. All other information e.g. noise or changes in light intensity that do not cause the light intensity to pass through a threshold could be ignored. The transitions that pass through the threshold may be presented on a computer monitor.

The combination of the ground glass/fresnel lens assembly 27 and camera, as described herein, may be replaced with other systems for recording light e.g. a photodiode array of the size of the image plane, with the diode spacing being less than e.g. 100 $\mu$m.

Many defects produce characteristic spectra in the light that is detected. For instance, a bubble tends to produce a dark central region but outer halo effects that often are shaped in the form of opposed crescents. A solid particle on a surface tends to produce a darkened region, whereas a defect resulting from a cold particle of glass in the molten glass that is cast tends to produce a central light spot with two areas on the edges that are of diminished brightness. In many instances, the particular defect particle may be smaller than a pixel in the camera used to detect the light, but the resultant edge effects may produce an image that is detectable and recognizable.

A sheet of glass cut for a particular end-use, for example the window on the side of an automobile, may be of a complicated shape and may additionally have holes therein that are used in movement of the window. The method of the present invention can confirm the exact location of the holes and the particular shape of the piece of glass. Moreover, such glass is normally ground to remove the sharp edges, and this produces a characteristic edge pattern. In the event that the grinding wheels used to grind the edges of the glass are not aligned or of poor quality, characteristic patterns deviating from the normal pattern may be formed, which may be recognized and identify process problems. In addition, the grinding may produce chips along the edges of the section that has been ground or small cracks known as vents, which typically appear in the corners of the ground glass sheet. Logos or other writings on the glass may be identified, and the integrity can be confirmed. Many automobile windows have heating and/or antenna strips located within the glass, and the method of the present invention may be used to detect broken sections of the heating or antenna strips. Bright field illumination typically does not detect scratches or dust particles, which are typically of less than 10 microns in size i.e. below the pixel resolution, and normally will not detect lint or hair both of which tend to have point contact on the glass and hence are of small size. Dark field illumination is used to detect scratches.

The position of the glass within the glass inspection system is not important, provided that it is located within the width of the laser beam. Moreover, the method of the present invention is capable of being used with curved glass, as the sheets of light pass straight through such glass. Computer software may be used to more precisely show the location of defects in curved glass.

Some sections of the glass inspection system, particularly the lasers and cylindrical lens system, may be sealed units to inhibit the presence of dust. However, other sections of the glass inspection system are susceptible to the presence of dust. For this reason, the glass inspection system is operated with an air pressure slightly above atmospheric pressure so that there is a gentle flow of air outwards from the glass inspection system, to inhibit dust particles being brought into the glass inspection system. In addition, the air circulated within the glass inspection system is passed through at least one HEPA filter, as well as electronic filters, with the air being exchanged frequently e.g. every five minutes.

Time delayed integration techniques may be used in the detection and analysis of the images that are acquired.

The present invention has been particularly described with reference to one laser being used for bright field illumination and one laser being used for dark field illumination. The use of dark field illumination is an important aspect of the present invention, in that it is particularly useful for detection of scratches on the glass. Scratches are normally not seen under bright field illumination. In detection of dark field illumination, it is preferred that a light stop i.e. a spatial filter, be used to inhibit the passage of light at the most intense part of the light beam that is focused on the camera. Such light is not required for detection of scratches, and moreover would swamp the variations of light that would reflect the presence of scratches.

The glass inspection system may be capable of being used with glass up to about 250 mm in width. However in many instances, samples of glass of wider widths e.g. up to 450 mm in width may need to be inspected. In this event, two lasers may be used in conjunction to provide a broader bright field illumination. This may be achieved through use of a dual lens system or a multi-lens system, aligned and typically bonded together so that edge effects where the lens are bonded are minimal, or most preferably in which the dual or multi-lenses are disposed in a manner similar to tiles overlapping at their edges, to provide a lens system of a required width, with software being used to compensate for overlap of lenses. Similarly, two lasers are used for dark field illumination and typically located on opposed sides of the two lasers used for bright field illumination so that the dark field illumination may be focused to a single camera. The use of a single camera for each of bright field illumination and dark field illumination simplifies analysis of the results. It is understood that further lasers could be added, if necessary.

It is believed that interference patterns maybe used to indicate the presence of distortions and other irregularities in the flatness of the sheet of glass.

The present invention provides a versatile glass inspection system and method for inspection of glass, and which is capable of simultaneously identifying a wide variety of defects by type, magnitude and location, in a manner that not only permits identification of glass that does not meet product specification but also assists in identifying the causes of the defects.

What is claimed is:

1. An inspection system for a sheet of glass, comprising:
   a) a first laser and a second laser, each of the first laser and second laser providing a sheet of light;
   b) a cylindrical lens system, said lens system having a focal point on the main optical axis thereof;
   c) a first light detection system and a second light detection system;
      the first laser being located at the focal point of the lens system, the second laser being located at a distance from the lens system that is greater than that of the first laser, said second laser being located off of the axis of the lens system and focused at the second detection system, said second detection system having a spatial filter,
      the first light detection system receiving light from the first laser and the second light detection system receiving light from the second laser;
      the inspection system being adapted to position a sheet of glass between the lens system and the detection systems.

2. The inspection system of claim 1 in which the first light detection system has a semi-transparent screen and a fresnel lens, and a camera focused on the surface of the screen, and in which the second light detection system comprises a camera with a spatial filter.

3. The inspection system of claim 1 further comprising a computer communicating with said first light detection system and said second light detection system, said computer executing software to determine the location, type and magnitude of defects in the sheet of glass based on image data captured by said first light detection system and said second light detection system.

4. The inspection system of claim 2 further comprising a computer communicating with said first light detection system and said second light detection system, said computer executing software to determine the location, type and magnitude of defects in the sheet of glass based on image data captured by said first light detection system and said second light detection system.

5. The inspection system of claim 3 wherein said computer records the location, type and magnitude of defects in the sheet of glass.

6. The inspection system of claim 5 wherein said computer includes a monitor and wherein said software generates a defect map showing the location, type and magnitude of defects in the sheet of glass for display on said monitor.

7. The inspection system of claim 4 wherein said computer records the location, type and magnitude of defects in the sheet of glass.

8. The inspection system of claim 7 wherein said computer includes a monitor and wherein said software generates a defect map showing the location, type and magnitude of defects in the sheet of glass for display on said monitor.

9. The inspection system of claim 1 including at least two cylindrical lens systems, at least two first lasers and at least two second lasers, wherein each of the first lasers is located at the focal point of a respective one of the cylindrical lens systems and each of the second lasers is located at a distance from a respective other of the cylindrical lens systems that is greater than that of the first lasers, each said second laser being located off of the axis of the respective cylindrical lens system, the first and second lasers being positioned such that light from both of the first lasers is detected by the first light detection system and light from both of the second lasers is detected by the second light detection system.

10. An inspection system for a sheet of glass, comprising:
   a) a first source of light generating bright field illumination in the form of a collimated sheet of light that is passed through said sheet of glass and means to detect said bright field illumination after having passed through said sheet of glass; and
   b) a second source of light generating dark field illumination in the form of a converging sheet of light that is passed through said sheet of glass and means to detect the dark field illumination after having passed through said sheet of glass.

11. A method for inspection of a sheet of glass, comprising the steps of:
   a) providing bright field illumination of a sheet of glass in the form of a collimated sheet of light and detecting said bright field illumination thus obtained;
   b) providing dark field illumination of a sheet of glass in the form of a converging sheet of light and detecting said dark field illumination thus obtained; and
   c) analyzing said obtained bright field illumination and said dark field illumination for presence of defects in said sheet of glass.

12. The method of claim 11 in which said bright field illumination and said dark field illumination are detected by capturing images thereof, said images being analyzed by a computer executing software thereby to determine the presence of defects in said sheet of glass.

13. The method of claim 11 wherein said computer analyzes said images to detect defects having a size of greater than 100 microns.

14. A method for inspection of a sheet of glass for defects therein, in an apparatus that includes a first laser and a second laser, each of the first laser and second laser providing a sheet of light; a cylindrical lens system, said lens system having a focal point on the main optical axis thereof; and a first light detection system and a second light detection system, said method comprising the steps of:

passing light from the first laser located at the focal point of the cylindrical lens system and from the second laser located at a distance from the cylindrical lens system that is greater than that of the first laser through said cylindrical lens system, said second laser being located off of the axis of the cylindrical lens system, the light from the first laser being collimated light, passing said light through a sheet of glass to be inspected;

detecting light from the first laser with the first light detection system; and detecting light from the second laser with the second light detection system.

15. The method of claim 14 further comprising the step of inhibiting intense light from being detected by said second light detection system.

16. The method of claim 15 wherein said inhibiting is performed by a spatial filter.

17. An inspection system according to claim 10 wherein said first source of light and said second source of light are lasers.

18. An inspection system according to claim 17 wherein said means to detect bright field illumination is a first camera and wherein said means to detect dark field illumination is a second camera.

19. An inspection system according to claim 18 wherein said bright field illumination passes through a lens assembly after having passed through said sheet of glass and prior to impinging on said first camera.

20. An inspection system according to claim 19 wherein said lens assembly includes a semi-transparent screen and a fresnel lens, said fresnel lens being positioned between said semi-transparent screen and said first camera, said first camera being focused on the surface of the semi-transparent screen.

21. An inspection system according to claim 18 wherein said dark field illumination passes through a spatial filter prior to impinging on said second camera.

22. An inspection system according to claim 21 wherein said spatial filter is provided on an objective lens of said second camera.

23. An inspection system according to claim 22 wherein said spatial filter is an opaque dot concentrically positioned on said objective lens.

24. An inspection system according to claim 18 further comprising a processor in communication with said first camera and said second camera, said processor receiving image data from said first camera and said second camera and processing said image data to detect the presence of defects in said sheet of glass.

25. An inspection system according to claim 24 wherein said processor compares said image data with thresholds to detect the presence of defects in said sheet of glass.

26. An inspection system according to claim 25 wherein said processor compares said image data with a first threshold to detect defects that obstruct the passage of light through said sheet of glass and a second threshold to detect the presence of edge effects of bubbles in said sheet of glass.

27. An inspection system according to claim 25 wherein said processed image data is displayed on a computer monitor as a map showing detected defects.

28. An inspection system according to claim 27 wherein said detected defects are displayed on said map as icons, said icons being selectable to present characteristics of said detected defects.

29. An inspection system according to claim 28 wherein the shapes of said icons represent the types of the detected defects.

30. An inspection system according to claim 29 wherein the colors of said icons represent the sizes of the detected defects.

31. An inspection system for a sheet of glass, comprising:

a conveyor system transporting a sheet of glass;

a first light generating system generating a collimated sheet of light that is passed through said sheet of glass;

a second light generating system generating a converging sheet of light that is passed through said sheet of glass;

a first light detection system detecting the collimated light after the collimated sheet of light has passed through said sheet of glass; and a second light detection system detecting the converging light after the converging sheet of light has passed through said sheet of glass.

32. An inspection system according to claim 31 wherein said first and second light generating systems are located on one side of said conveyor system and wherein said first and second light detection systems are located on an opposite side of said conveyor system.

33. An inspection system according to claim 32 wherein said conveyor system includes a pair of conveyor sections, said conveyor sections being spaced apart longitudinally to define a light window therebetween, said collimated sheet of light and said converging sheet of light passing through said sheet of glass and through said window.

34. An inspection system according to claim 33 wherein said first and second light generating systems and said first and second light detection systems are accommodated by a housing through which said conveyor system extends, said housing being pressurized to inhibit dust from entering said housing.

35. An inspection system according to claim 34 wherein said housing includes an upper housing above said conveyor system accommodating one of said first and second light generating systems and said first and second light detection systems and a lower housing below said conveyor system and accommodating another of said first and second light generating systems and said first and second light detection systems.

36. An inspection system according to claim 31 wherein said first light generating system includes a first laser and a cylindrical lens system having a focal point on a main optical axis thereof and wherein said second light generating system includes a second laser and said cylindrical lens system.

37. An inspection system according to claim 36 wherein said first laser is located at the focal point of said cylindrical lens system and wherein said second laser is located at a distance from said cylindrical lens system that is greater than that of said first laser, said second laser being located off of the main optical axis of said cylindrical lens system and focused at the second light detection system.

38. An inspection system according to claim 37 wherein said second light detection system includes a spatial filter and a camera.

39. An inspection system according to claim 38 wherein said spatial filter is provided on an objective lens of said camera.

40. An inspection system according to claim 39 wherein said spatial filter is an opaque dot concentrically positioned on said objective lens.

41. An inspection system according to claim 37 wherein said first light detection system includes a lens assembly and a camera spaced from said lens assembly.

42. An inspection system according to claim 41 wherein said lens assembly includes a semi-transparent screen and a fresnel lens, said fresnel lens being positioned between said semi-transparent screen and said camera, said camera being focused on the surface of the semi-transparent screen.

43. An inspection system according to claim 42 wherein said first light detection system further includes a folding mirror disposed between said lens assembly and said camera.

44. An inspection system according to claim 31 further comprising a processor in communication with said first and second light detection systems, said processor receiving image data from said first and second light detection systems and processing said image data to detect the presence of defects in said sheet of glass.

45. An inspection system according to claim 44 wherein said processor compares said image data with thresholds to detect the presence of defects in said sheet of glass.

46. An inspection system according to claim 45 wherein said processor compares said image data with a first threshold to detect defects that obstruct the passage of light through said sheet of glass and a second threshold to detect the presence of edge effects of bubbles in said sheet of glass.

47. An inspection system according to claim 45 wherein said processed image data is displayed on a computer monitor as a map showing detected defects.

48. An inspection system according to claim 47 wherein said detected defects are displayed on said map as icons, said icons being selectable to present characteristics of said detected defects.

49. An inspection system according to claim 48 wherein the shapes of said icons represent the types of the detected defects.

50. An inspection system according to claim 49 wherein the colors of said icons represent the sizes of the detected defects.

* * * * *

UNITED STATES PATENT AND TRADEMARK OFFICE
CERTIFICATE OF CORRECTION

PATENT NO. : 6,437,357 B1 Page 1 of 3
DATED : August 20, 2002
INVENTOR(S) : Weiss et al.

It is certified that error appears in the above-identified patent and that said Letters Patent is hereby corrected as shown below:

Drawings,
Figure 1, replace "8D" with -- 21 --; replace "10" with -- 24 --; replace "8B" with -- 20 --, replace "9" with -- 22 --; replace "15A" with -- 30A --; replace "16A" with -- 31A --; replace "16" with -- 31A --; replace "15" with -- 30A --; replace "14" with -- 29 --; replace "13" with -- 28 --; add ref nos. 5, 9, 36, and 38 (as shown below)

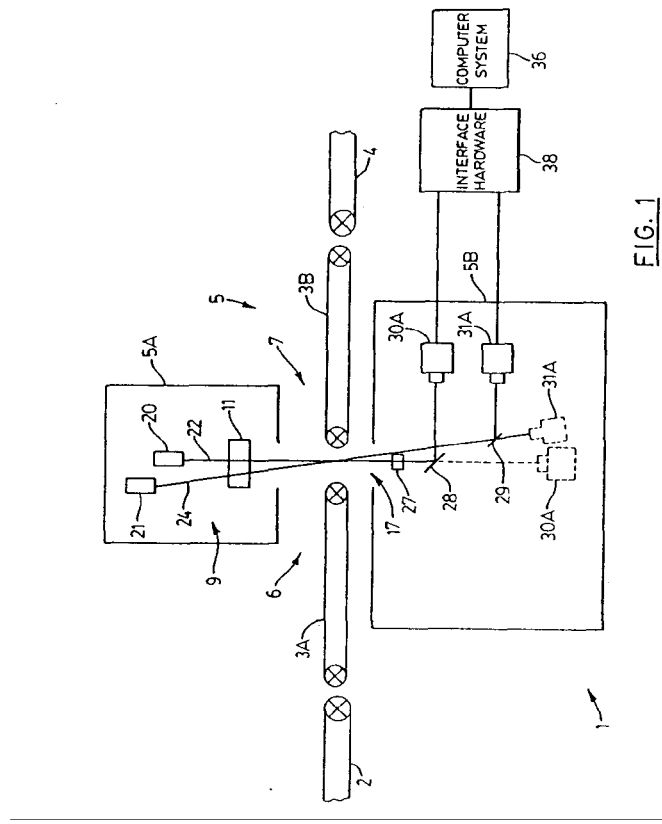

UNITED STATES PATENT AND TRADEMARK OFFICE
CERTIFICATE OF CORRECTION

PATENT NO. : 6,437,357 B1
DATED : August 20, 2002
INVENTOR(S) : Weiss et al.

It is certified that error appears in the above-identified patent and that said Letters Patent is hereby corrected as shown below:

Drawings,
Figure 2, replace "22" with -- 24 --; replace "24" with -- 22 --; replace "5" with -- 9 --; replace "30" with -- 30A --; replace "31" with -- 31A --; please add ref nos. 11 and 31B (as shown below)

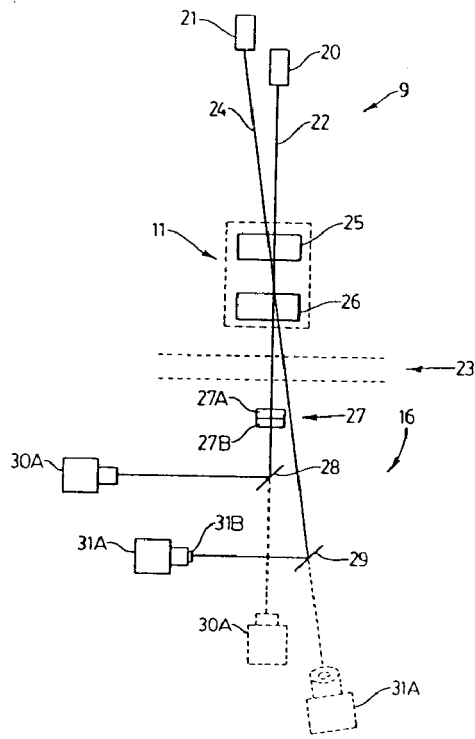

FIG. 2

UNITED STATES PATENT AND TRADEMARK OFFICE
CERTIFICATE OF CORRECTION

PATENT NO. : 6,437,357 B1
DATED : August 20, 2002
INVENTOR(S) : Weiss et al.

It is certified that error appears in the above-identified patent and that said Letters Patent is hereby corrected as shown below:

Drawings,
Figure 3, replace "22A" with -- 24A --; replace "24A" with -- 22A --; replace "22B" with -- 24B --; and replace "24B" with -- 22B -- (as shown below)

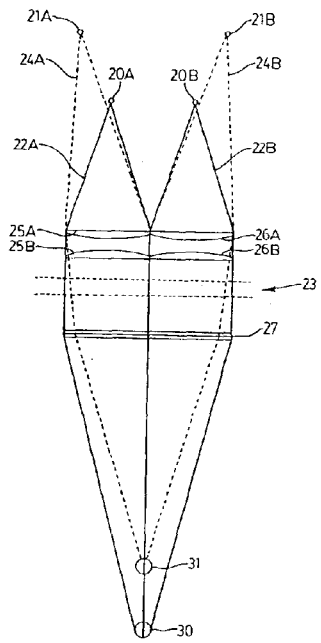

FIG. 3

Signed and Sealed this

Tenth Day of August, 2004

JON W. DUDAS
*Acting Director of the United States Patent and Trademark Office*